(12) United States Patent
Cong et al.

(10) Patent No.: US 10,279,049 B2
(45) Date of Patent: May 7, 2019

(54) ANTIBODY-DRUG CONJUGATES OF TUBULYSIN ANALOGS WITH ENHANCED STABILITY

(71) Applicant: BRISTOL-MYERS SQUIBB COMPANY, Princeton, NJ (US)

(72) Inventors: Qiang Cong, Palo Alto, CA (US); Sanjeev Gangwar, Foster City, CA (US); Vangipuram S. Rangan, Pleasant Hill, CA (US); Mei-Chen Sung, Milpitas, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 120 days.

(21) Appl. No.: 15/587,927

(22) Filed: May 5, 2017

(65) Prior Publication Data

US 2017/0326247 A1 Nov. 16, 2017

Related U.S. Application Data

(60) Provisional application No. 62/333,924, filed on May 10, 2016.

(51) Int. Cl.
*A61K 39/395* (2006.01)
*A61K 47/68* (2017.01)
*C07K 16/28* (2006.01)

(52) U.S. Cl.
CPC ...... *A61K 47/6803* (2017.08); *A61K 47/6811* (2017.08); *A61K 47/6851* (2017.08); *C07K 16/28* (2013.01); *C07K 2317/565* (2013.01); *C07K 2317/94* (2013.01)

(58) Field of Classification Search
None
See application file for complete search history.

(56) References Cited

U.S. PATENT DOCUMENTS

| 8,268,970 B2 | 9/2012 | Terrett et al. |
| 8,394,922 B2 | 3/2013 | Cheng et al. |
| 8,980,824 B2 | 3/2015 | Cong et al. |
| 2013/0309256 A1 | 11/2013 | Lyon et al. |

FOREIGN PATENT DOCUMENTS

| WO | WO 2015/057699 A2 | 4/2015 |
| WO | WO 2016/040684 A1 | 3/2016 |

OTHER PUBLICATIONS

Ranganathan Balasubramanian, et al., "Total Synthesis and Biological Evaluation of Tubulysin U, Tubulysin V, and Their Analogues," *Journal of Medicinal Chemistry*, vol. 52, No. 2, pp. 238-240, 2009.
Alexander Domling, et al., "Total Synthesis of Tubulysin U and V," *Angewandte Chem Int. Ed.*, vol. 45, pp. 7235-7239, 2006.
Jagath R. Junutula, et al., "Site-Specific Conjugation of a Cytotoxic Drug to an Antibody Improves the Therapeutic Index," *Nature Biotechnology*, vol. 26, No. 8, pp. 925-932, 2008.
Gurmeet Kaur, et al., "Biological Evaluation of Tubulysin A: a Potential Anticancer and Antiangiogenic Natural Product," *Biochem J.*, vol. 396, pp. 235-242, 2006.
Mohamed W. Khalil, et al., "Mechanism of Action of Tubulysin, an Antimitotic Peptide from Myxobacteria," *ChemBioChem*, vol. 7, pp. 678-683, 2006.
David Schrama, et al., "Antibody Targeted Drugs as Cancer Therapeutics," *Nature Review Drug Discovery*, vol. 5, pp. 147-159, 2006.
International Search Report and Written Opinion, for PCT Application No. PCT/US2017/030760, dated Jul. 27, 2017.

*Primary Examiner* — Sheela J. Huff
(74) *Attorney, Agent, or Firm* — Yuan Chao

(57) ABSTRACT

The drug component of an antibody-drug conjugate having a structure according to formula (II), where Ab, m, n, $R^1$, $R^2$, $R^3$, $R^4$, and $R^5$ are as defined in the application, exhibits unexpectedly improved stability.

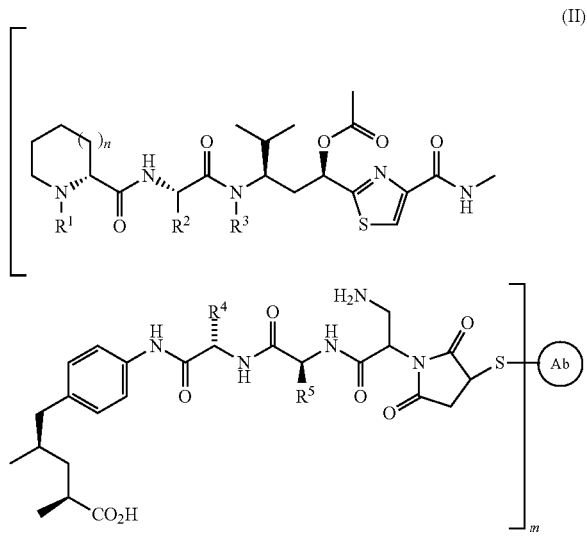

15 Claims, 5 Drawing Sheets
Specification includes a Sequence Listing.

FIG. 3

Anti-mesothelin antibody 6A4 heavy chain variable region

```
Gln Val His Leu Val Glu Ser Gly Gly Val Val Gln Pro Gly Arg
1               5                   10                  15
                                                          CDR1
                                                          ~~~~~~~
Ser Leu Arg Leu Ser Cys Val Ala Ser Gly Ile Thr Phe Arg Ile Tyr
            20                  25                  30

~~~~~~~~~~~
Gly Met His Trp Val Arg Gln Ala Pro Gly Lys Gly Leu Glu Trp Val
            35                  40                  45
                                    CDR2
            ~~~~~~~~~~~~~~~~~~~~~~~~~~~~~~~~~~~~~~~~~~~~~~~~~~~
Ala Val Leu Trp Tyr Asp Gly Ser His Glu Tyr Tyr Ala Asp Ser Val
            50              55                  60
~~~
Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Ile Tyr Tyr Cys
                85                  90                  95
                                    CDR3
                    ~~~~~~~~~~~~~~~~~~~~~~~~~~~~~~~~~~~~~~~~~~~
Ala Arg Asp Gly Asp Tyr Tyr Asp Ser Gly Ser Pro Leu Asp Tyr Trp
            100                 105                 110

Gly Gln Gly Thr Leu Val Thr Val Ser Ser
            115             120
```

FIG. 4

Anti-mesothelin antibody 6A4 kappa chain variable region

```
Glu Ile Val Leu Thr Gln Ser Pro Ala Thr Leu Ser Leu Ser Pro Gly
1               5                   10                  15

CDR1
                                    ~~~~~~~~~~~~~~~~~~~~~~~~~~~~
Glu Arg Ala Thr Leu Ser Cys Arg Ala Ser Gln Ser Val Ser Ser Tyr
                20                  25                  30

~~~~~~~
Leu Ala Trp Tyr Gln Gln Lys Pro Gly Gln Ala Pro Arg Leu Leu Ile
            35                  40                  45

CDR2
    ~~~~~~~~~~~~~~~~~~~~~~~~~~~~
Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

CDR3
                                    ~~~~~~~~~~~~~~~~~~~~~~~~~~~~
Glu Asp Phe Ala Val Tyr Tyr Cys Gln Gln Arg Ser Asn Trp Pro Leu
                85                  90                  95

~~~
Thr Phe Gly Gly Gly Thr Lys Val Glu Ile Lys
            100                 105
```

ANTIBODY-DRUG CONJUGATES OF TUBULYSIN ANALOGS WITH ENHANCED STABILITY

CROSS-REFERENCE TO RELATED APPLICATIONS

This application claims the benefit under 35 U.S.C. § 119(e) of U.S. Provisional Application Ser. No. 62/333,924; filed May 10, 2016; the disclosure of which is incorporated herein by reference.

SEQUENCE LISTING

Incorporated herein by reference in its entirety is a Sequence Listing named "20170309_SEQT_12733USN-P_YC.txt," comprising SEQ ID NO:1 through SEQ ID NO:8, which include nucleic acid and/or amino acid sequences disclosed herein. The Sequence Listing has been submitted herewith in ASCII text format via EFS-Web, and thus constitutes both the paper and computer readable form thereof. The Sequence Listing was first created using PatentIn 3.5 on Mar. 14, 2016, and is approximately 4 KB in size

BACKGROUND OF THE INVENTION

This invention relates to antibody-drug conjugates of tubulysin analogs having enhanced stability, tubulysin analog-linker compounds for making such antibody-drug conjugates, methods for preparing such antibody-drug conjugates and for their use.

A type of anticancer agent that is generating strong interest is an antibody-drug conjugate (ADC, also referred to as an immunoconjugate). In an ADC, a therapeutic agent, also referred to as the drug, cytotoxin, payload, or warhead, is covalently linked to an antibody whose antigen is expressed by a cancer cell (tumor associated antigen). The moiety covalently linking the antibody and the drug is referred to as the linker. In the case where each antibody has one drug attached to it, the structure of an ADC can be generally represented as:

[Antibody]-[Linker]-[Drug]

The antibody, by binding to the antigen, delivers the ADC to the cancer site. There, cleavage of the linker or degradation of the antibody leads to the release of the therapeutic agent. Conversely, while the ADC is circulating in the blood system, the therapeutic agent is held inactive because of its covalent linkage to the antibody. Thus, the therapeutic agent used in an ADC can be much more potent (i.e., cytotoxic) than ordinary chemotherapy agents because of its localized release. For a review on ADCs, see Schrama et al. 2006. (The full bibliographic citation for this and other documents cited herein by first author or inventor and year are listed at the end of this specification.)

One class of compounds that has been proposed as the drug in an ADC are tubulysin analogs. The tubulysins are anti-mitotic naturally occurring cytotoxins, first isolated from myxobacteria cultures. During mitosis, a cell's microtubules reorganize to form the mitotic spindle, a process requiring the rapid assembly and disassembly of microtubules from their constituent proteins α- and β-tubulin. The cytotoxicity of the tubulysins derives from their ability to prevent the assembly of the tubulins into microtubules, causing the affected cells to accumulate in the $G_2/M$ phase and undergo apoptosis (Khalil et al. 2006).

The tubulysins have a tetrapeptidyl scaffold consisting of one proteinogenic and three non-proteinogenic amino acid subunits as shown in formula (A): N-methylpipecolinic acid (Mep), isoleucine (Ile), tubuvaline (Tuv), and either tubuphenylalanine (Tup, R' equals H) or tubutyrosine (Tut, R' equals OH). Structural variations among the tubulysins (named A, B, etc.) center around residues R', R" and R'" of formula (A), as shown in Table I.

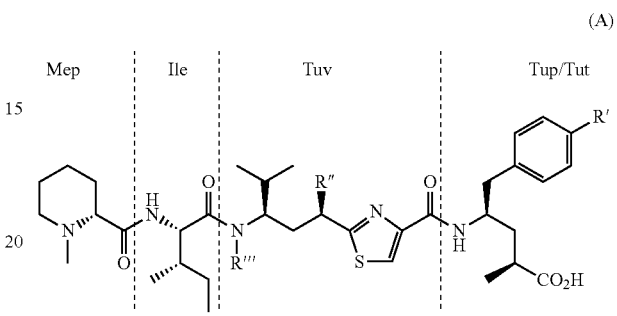

(A)

TABLE I

Naturally Occurring Tubulysins

| Tubulysin | R' | R" | R'" |
|---|---|---|---|
| A | OH | OC(=O)Me | $CH_2OC(=O)$i-Bu |
| B | OH | OC(=O)Me | $CH_2OC(=O)$n-Pr |
| C | OH | OC(=O)Me | $CH_2OC(=O)$Et |
| D | H | OC(=O)Me | $CH_2OC(=O)$i-Bu |
| E | H | OC(=O)Me | $CH_2OC(=O)$n-Pr |
| F | H | OC(=O)Me | $CH_2OC(=O)$Et |
| G | OH | OC(=O)Me | $CH_2OC(=O)CH=CH_2$ |
| H | H | OC(=O)Me | $CH_2OC(=O)$Me |
| I | OH | OC(=O)Me | $CH_2OC(=O)$Me |
| U | H | OC(=O)Me | H |
| V | H | OH | H |
| Y | OH | OC(=O)Me | H |
| Z | OH | OH | H |
| Pretubulysin | H | H | Me |

Cheng et al. 2013 disclose ADCs of tubulysin analogs, in particular analogs having at the R' position of formula (A) above an amino ($NH_2$) group, which can serve as an attachment site for the linker.

The acetate group in the Tuv subunit appears to be essential for biological activity. Its removal (deacetylation), resulting in compounds in which R" in formula (A) is hydroxyl, reportedly leads to loss of biological activity (Domling et al. 2006). In a study of tubulysins U and V, which differ in the former being acetylated and the latter being deacetylated, tubulysin V was reported to be less potent by about 200× to 600×, depending on the assay (Balasubramanian et al. 2009). Because an acetate group can be susceptible to hydrolysis, deacetylation at the R" position is a concern in the development of tubulysin analogs as the drug in an ADC. If deacetylation occurs, cleavage of the linker would lead to release of an inactive drug.

Cong et al. 2015 have proposed addressing this issue by replacing the naturally occurring acetate group in the Tuv subunit with a more hydrolytically resistant moiety such as a carbamate:

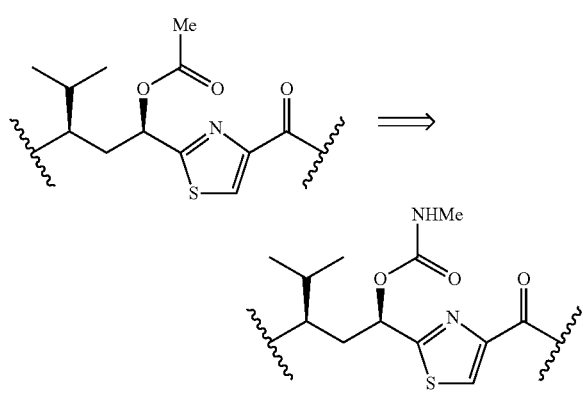

However, in a field as complex as the development of pharmaceuticals, a tubulysin analog having carbamate group in the Tuv subunit will not necessarily function identically to an analog having the naturally occurring acetate group in each and every instance. Therefore, it is desirable to develop a solution to the issue of acetate hydrolysis, in which the acetate group is preserved, as an alternative for those instances in which the pharmaceutical properties of the carbamate group are not entirely coincident with those of the acetate group.

BRIEF SUMMARY OF THE INVENTION

We have discovered that, unexpectedly, the resistance to hydrolysis of the Tuv acetate group in an ADC can be enhanced by appropriate linker design. Even more unexpectedly, the moiety on the linker resulting in such enhancement is located distally from the acetate group.

Typically, an ADC is prepared by first making the drug-linker compound using medicinal chemistry techniques and the antibody using recombinant protein expression techniques. Next, the drug-linker compound is conjugated to the antibody in an aqueous medium.

A preferred linker for ADCs containing a tubulysin analog comprises an enzymatically cleavable polypeptide and a maleimide group. An illustrative tubulysin analog-linker compound (B) having such a linker, from Cheng et al. 2013, is shown below:

In this structure, the valine-citrulline dipeptide (Val-Cit, written in the conventional N→C direction), is a substrate for the enzyme cathepsin B, which is found inside lysosomes of the target cancer cells, while the maleimide group readily reacts in an aqueous medium with a sulfhydryl (SH) group on an antibody Ab to form the ADC, in a Michael addition reaction:

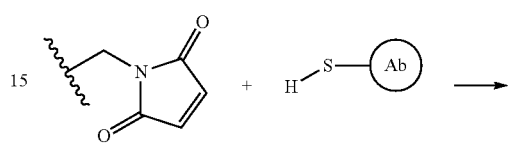

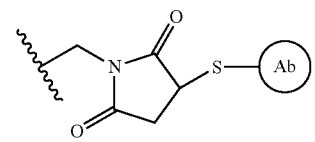

We have discovered that modifying the linker by locating a methyleneamino ($CH_2NH_2$) group adjacent to the maleimide group has the unexpected effect of stabilizing the Tuv acetate group against hydrolysis:

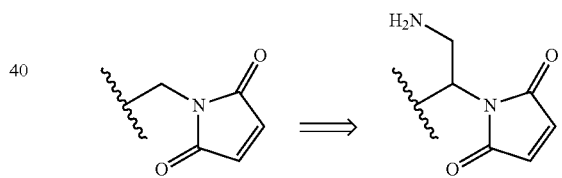

Thus, in one aspect, this invention provides a tubulysin analog-linker compound having a structure represented by formula (I)

(B)

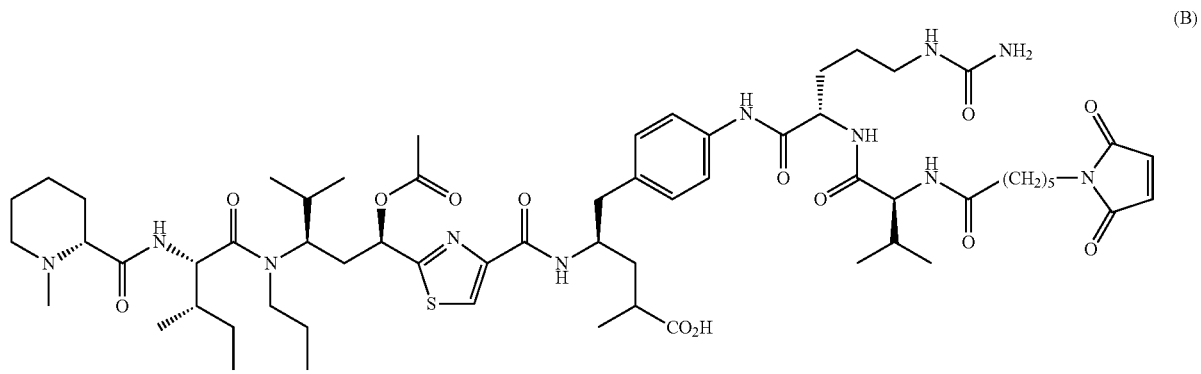

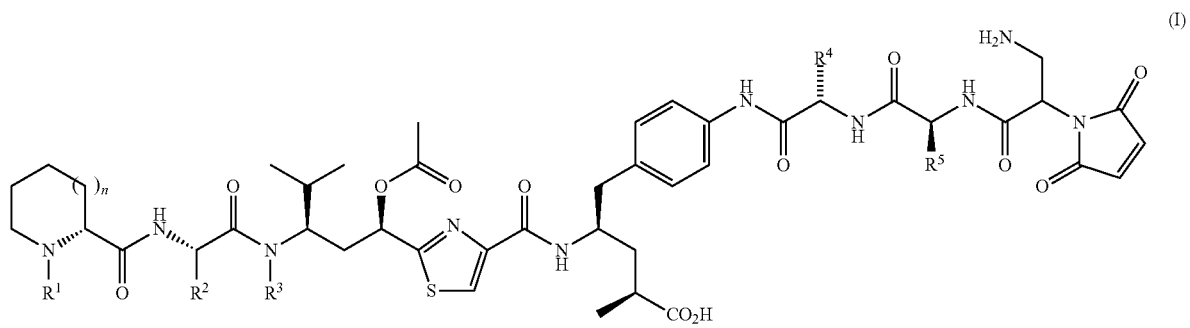

(I)

wherein n is 0, 1, or 2;

$R^1$ is H, Me, Et, or n-Pr;

$R^2$ is Me, Et, $CH_2CH_2CH_3$, $CH(Me)_2$, $CH(Et)_2$, or

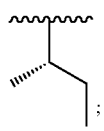 [SMILES: *[C@@H](C)CC]

$R^3$ is H, $C_1$-$C_5$ alkyl, $C_1$-$C_5$ alkenyl, $C_1$-$C_5$ alkynyl, $CH_2OC(\!=\!O)C_1$-$C_5$ alkyl, $CH_2OC(\!=\!O)C_1$-$C_5$ alkenyl, or $CH_2OC(\!=\!O)C_1$-$C_5$ alkynyl; and $R^4$ and $R^5$ are independently H, $CH_3$, $(CH_2)_3NHC(\!=\!NH)NH_2$, $CH_2C(\!=\!O)NH_2$, $CH_2CO_2H$, $(CH_2)_3NHC(\!=\!O)NH_2$, $CH_2SH$, $(CH_2)_2CO_2H$, $(CH_2)_2C(\!=\!O)NH_2$, $CH(CH_3)CH_2CH_3$, $CH_2CH(CH_3)_2$, $(CH_2)_4NH_2$, $(CH_2)_2SCH_3$, $(CH_2)_3CH_3$, $(CH_2)_3NH_2$, $CH_2C_6H_5$, $CH_2OH$, $CH(OH)CH_3$, $CH_2(p\text{-}C_6H_4OH)$, or $CH(CH_3)_2$;

or a pharmaceutically acceptable salt thereof.

In another aspect, this invention provides an antibody-drug conjugate having a structure represented by formula (II)

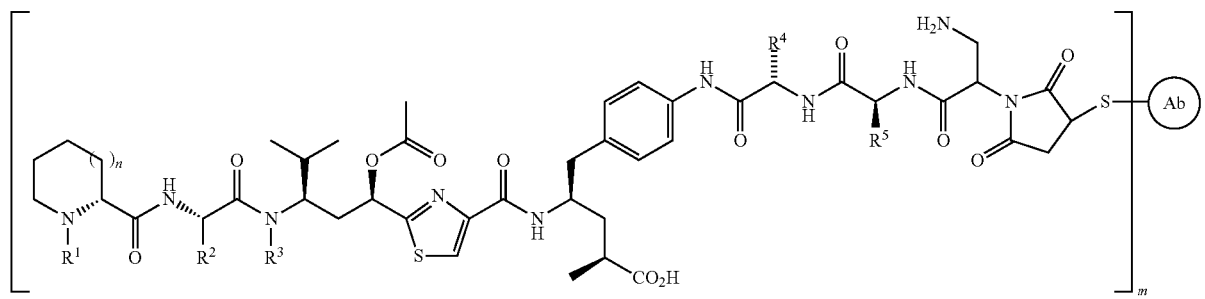

wherein m is 1, 2, 3, or 4;

Ab is an antibody; and n, $R^1$, $R^2$, $R^3$, $R^4$, and $R^5$ are as defined for formula (I).

BRIEF DESCRIPTION OF THE DRAWING(S)

FIGS. 3 and 4 show the heavy (SEQ ID NO:7) and kappa (SEQ ID NO:8) chain variable region amino acid sequences, respectively, of an antibody that can be used to make an ADC according to this invention.

DETAILED DESCRIPTION OF THE INVENTION

Definitions

Figure 1:
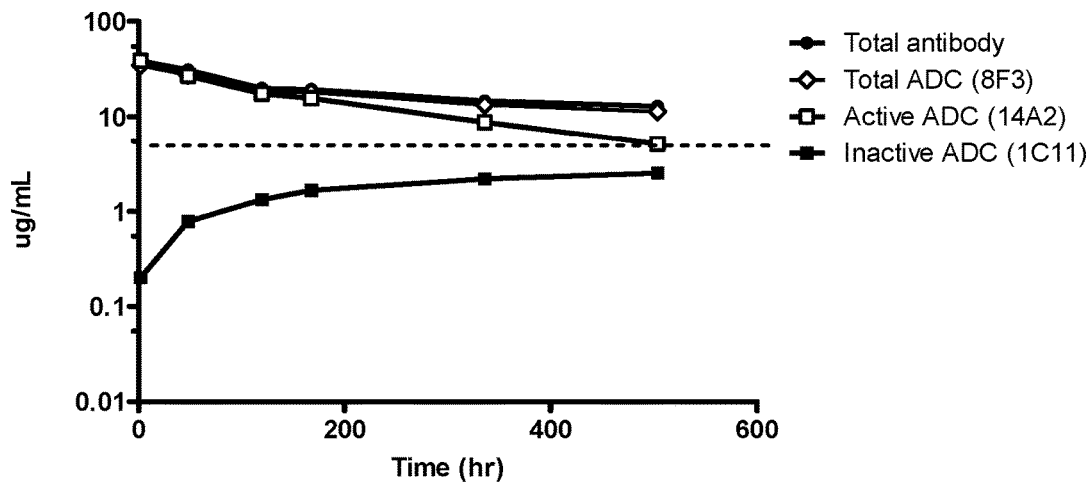
FIG. 1 is a graph showing the in vivo stability of an ADC according to this invention.

"Antibody" means whole antibodies and any antigen binding fragment (i.e., "antigen-binding portion") or single chain variants thereof. A whole antibody is a protein comprising at least two heavy (H) chains and two light (L) chains inter-connected by disulfide bonds. Each heavy chain comprises a heavy chain variable region ($V_H$) and a heavy chain constant region comprising three domains, $C_{H1}$, $C_{H2}$ and $C_{H3}$. Each light chain comprises a light chain variable region ($V_L$ or $V_k$) and a light chain constant region comprising one single domain, $C_L$. The $V_H$ and $V_L$ regions can be further subdivided into regions of hypervariability, termed complementarity determining regions (CDRs), interspersed with more conserved framework regions (FRs). Each $V_H$ and $V_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (Clq) of the classical complement system. An antibody is said to "specifically bind" to an antigen X if the antibody binds to antigen X with a $K_D$ of $5 \times 10^{-8}$ M or less, more preferably $1 \times 10^{-8}$ M or less, more preferably $6 \times 10^{-9}$ M or less, more preferably $3 \times 10^{-9}$ M or less, even more preferably $2 \times 10^{-9}$ M or less. The antibody can be chimeric, humanized, or, preferably, human. The heavy chain constant region can be engineered to affect glycosylation type or extent, to extend antibody half-life, to enhance or reduce interactions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antigen binding fragment" and "antigen binding portion" of an antibody (or simply "antibody portion" or "antibody fragment") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, for example, Abbas et al., *Cellular and Molecular Immunology*, 6th Ed., Saunders Elsevier 2007); (iv) a Fd fragment consisting of the $V_H$ and $C_{H1}$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Preferred antigen binding fragments are Fab, F(ab')$_2$, Fab', Fv, and Fd fragments. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv, or scFv); see, e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody.

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germline immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human antibody" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

"Aliphatic" means a straight- or branched-chain, saturated or unsaturated, non-aromatic hydrocarbon moiety having the specified number of carbon atoms (e.g., as in "$C_3$ aliphatic," "$C_{1-5}$ aliphatic," "$C_1$-$C_5$ aliphatic," or "$C_1$ to $C_5$ aliphatic," the latter three phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties). A similar understanding is applied to the number of carbons in other types, as in $C_{2-4}$ alkene, $C_4$-$C_7$ cycloaliphatic, etc. In a similar vein, a term such as "$(CH_2)_{1-3}$" is to be understand as shorthand for the subscript being 1, 2, or 3, so that such term represents $CH_2$, $CH_2CH_2$, and $CH_2CH_2CH_2$.

"Alkyl" means a saturated aliphatic moiety, with the same convention for designating the number of carbon atoms being applicable. By way of illustration, $C_1$-$C_4$ alkyl moieties include, but are not limited to, methyl, ethyl, propyl, isopropyl, isobutyl, t-butyl, 1-butyl, 2-butyl, and the like. "Alkylene" means a divalent counterpart of an alkyl group, such as $CH_2CH_2$, $CH_2CH_2CH_2$, and $CH_2CH_2CH_2CH_2$.

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl (vinyl), 2-propenyl (allyl or prop-2-enyl), cis-1-propenyl, trans-1-propenyl, E- (or Z-) 2-butenyl, 3-butenyl, 1,3-butadienyl (but-1,3-dienyl) and the like.

"Alkynyl" means an aliphatic moiety having at least one carbon-carbon triple bond, with the same convention for designating the number of carbon atoms being applicable. By way of illustration, $C_2$-$C_4$ alkynyl groups include ethynyl (acetylenyl), propargyl (prop-2-ynyl), 1-propynyl, but-2-ynyl, and the like.

Where a range is stated, as in "$C_1$-$C_5$ alkyl" or "5 to 10%," such range includes the end points of the range, as in $C_1$ and $C_5$ in the first instance and 5% and 10% in the second instance.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by this invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable ester" means an ester that hydrolyzes in vivo (for example in the human body) to produce the parent compound or a salt thereof or has per se activity similar to that of the parent compound. Suitable esters include $C_1$-$C_5$ alkyl, $C_2$-$C_5$ alkenyl or $C_2$-$C_5$ alkynyl esters, especially methyl, ethyl or n-propyl.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

In the formulae of this specification, a wavy line ($\sim\!\sim\!\sim$) transverse to a bond or an asterisk (*) at the end of the bond denotes a covalent attachment site. For instance, a statement that R is

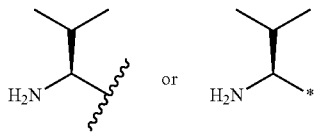

in the formula

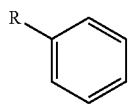

refers to

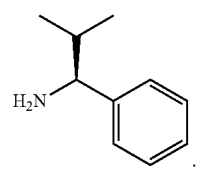

In the formulae of this specification, a bond traversing an aromatic ring between two carbons thereof means that the group attached to the bond may be located at any of the available positions of the aromatic ring. By way of illustration, the formula

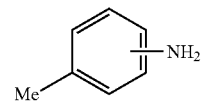

represents

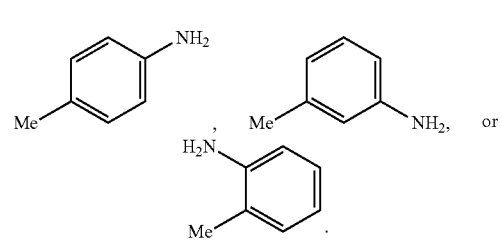

Effect of Methyleneamino ($CH_2NH_2$) Group

Lyon et al. 2013 noted that, although the addition of an antibody thiol group to a maleimide group to form an ADC occurs facilely, it is reversible in plasma to regenerate the maleimide group. In the absence of another thiol source, the maleimide can be recaptured by the antibody thiol to re-form the ADC. However, in the presence of a protein or peptide, such as serum albumin or glutathione, which can serve as an alternative thiol source, the maleimide can be diverted, resulting in loss of ADC:

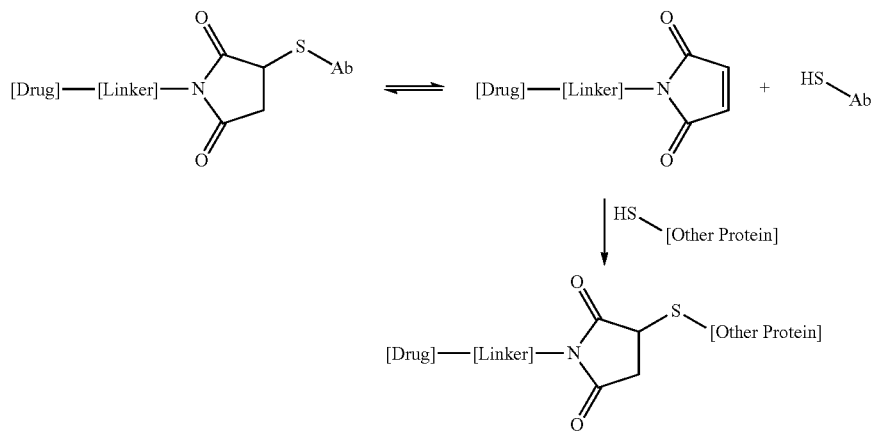

To address this issue, Lyon et al. 2013 placed a basic group such as a methyleneamino group near the thiol-substituted succinimide adduct in the ADC, to help catalyze its hydrolytic ring-opening to a seco structure that is not susceptible to reversal of the thiol addition, resulting in a stabilized linker and ADC. (Additionally, Lyon et al. 2015 disclose the same methyleneamino group, in the context of a PEGylated drug linker for improving conjugate pharmacokinetics.)

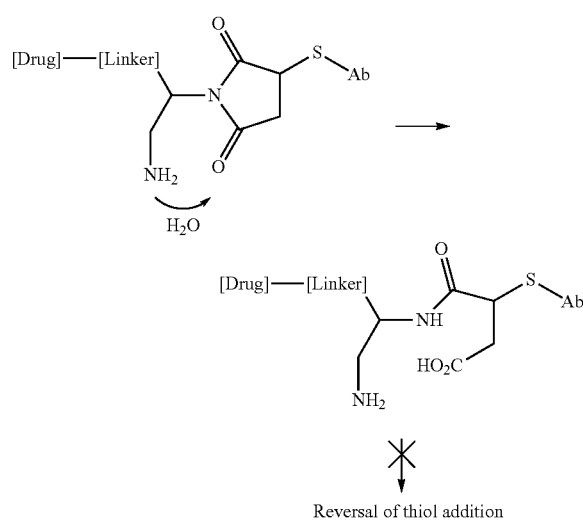

Reversal of thiol addition

The inventors here have discovered a different and unexpected beneficial effect of a similarly positioned methyleneamino group, which is not predictable from the disclosure of Lyon et al. 2013 and is in fact contraindicated by the chemistry taught therein. As shown by the data in the Examples hereinbelow (especially Example 1), the methyleneamino group, which per Lyon et al. 2013 promotes the hydrolysis of a nearby group, in this invention protects a distant group—the acetate of the Tuv subunit of a tubulysin analog—from hydrolysis.

Such an effect, acting at a distance, is surprising and unexpected, as neither the structures of the overall ADC, the linker, and the tubulysin analog, nor the results disclosed in Lyons et al. 2013 or 2015, suggest such a possibility.

Preferred Embodiments

In formulae (I) and (II), n preferably is 1.

In formulae (I) and (II), $R^1$ preferably is $CH_3$.

In formulae (I) and (II), $R^2$ preferably is Me, Et, n-Pr, i-Pr, or

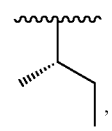

more preferably the latter.

In formulae (I) and (II), $R^3$ preferably is $C_1$-$C_3$ alkyl, more preferably $CH_3$ or $CH_2CH_2CH_3$.

The groups $R^4$ and $R^5$ in formulae (I) and (II) correspond to the side chain residue of various alpha-amino acids, some proteinogenic, some not: H (glycine), $CH_3$ (alanine), $(CH_2)_3NHC(=NH)NH_2$ (arginine), $CH_2C(=O)NH_2$ (asparagine), $CH_2CO_2H$ (aspartic acid), $(CH_2)_3NHC(=O)NH_2$ (citrulline), $CH_2SH$ (cysteine), $(CH_2)_2CO_2H$ (glutamic acid), $(CH_2)_2C(=O)NH_2$ (glutamine), $CH(CH_3)CH_2CH_3$ (isoleucine, for (S) configuration), $CH_2CH(CH_3)_2$ (leucine), $(CH_2)_4NH_2$ (lysine), $(CH_2)_2SCH_3$ (methionine), $(CH_2)_3CH_3$ (norleucine), $(CH_2)_2CH_3$ (norvaline), $(CH_2)_3NH_2$ (ornithine), $CH_2C_6H_5$ (phenylalanine), $CH_2OH$ (serine), $CH(OH)CH_3$ (threonine, for (R) configuration), $CH_2(p-C_6H_4OH)$ (tyrosine), or $CH(CH_3)_2$ (valine).

Preferably, in either formula (I) or (II), $R^4$ and $R^5$ are independently $CH(CH_3)_2$, $CH_3$, $(CH_2)_3NHC(=O)NH_2$, or $(CH_2)_4NH_2$. One preferred combination is $R^4$ equals $(CH_2)_3NHC(=O)NH_2$ and $R^5$ equals $CH(CH_3)_2$. Another preferred combination is $R^4$ equals $CH_3$ and $R^5$ equals $CH(CH_3)_2$.

A preferred tubulysin analog-linker compound according to this invention is represented by formula (Ia):

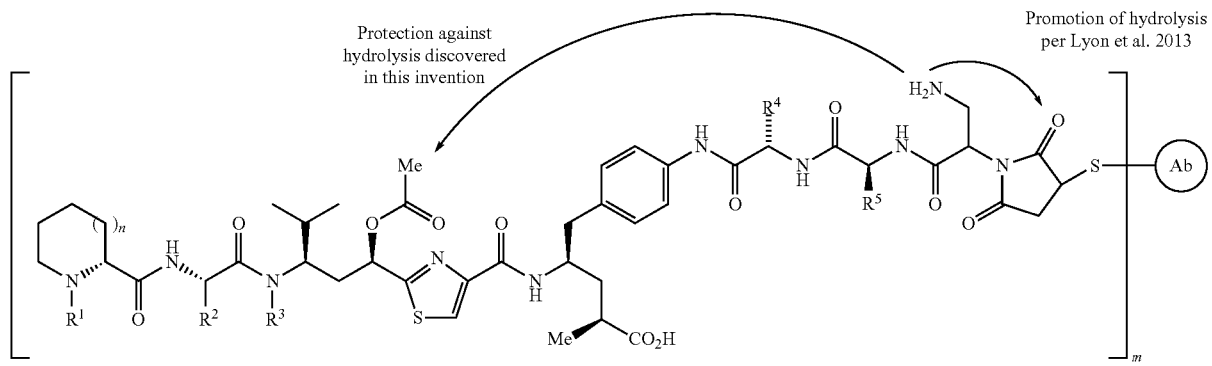

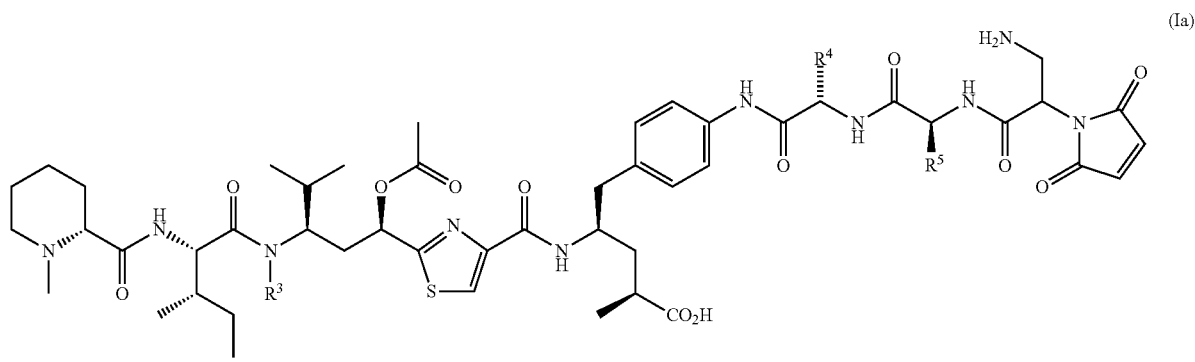

(Ia)

wherein
$R^3$ is $C_1$-$C_3$ alkyl, preferably $CH_3$ or $CH_2CH_2CH_3$, and more preferably $CH_3$; and
$R^4$ and $R^5$ are independently $CH(CH_3)_2$, $CH_3$, $(CH_2)_3NHC(=O)NH_2$, or $(CH_2)_4NH_2$, with one preferred combination being $R^4$ equals $(CH_2)_3NHC(=O)NH_2$ and $R^5$ equals $CH(CH_3)_2$ and another preferred combination being $R^4$ equals $CH_3$ and $R^5$ equals $CH(CH_3)_2$.

An ADC prepared from tubulysin analog-linker (Ia) is represented by formula (IIa)

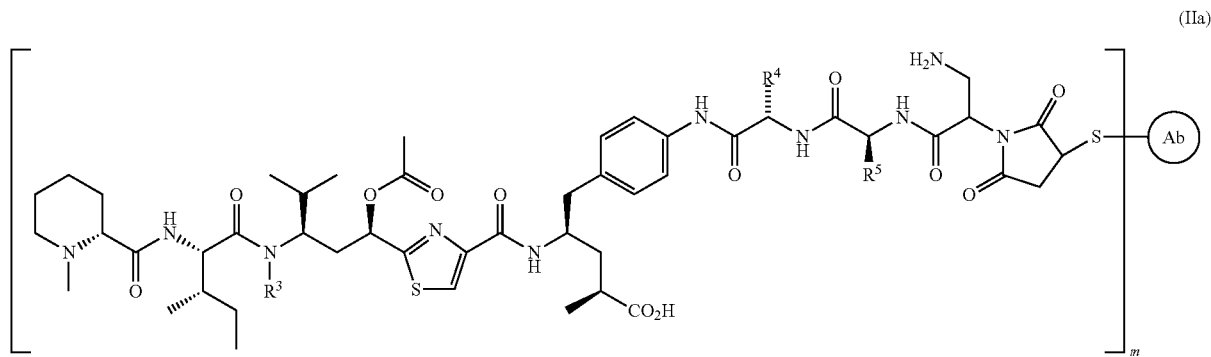

(IIa)

wherein
m is 1, 2, 3, or 4;
Ab is an antibody; and
$R^3$, $R^4$, and $R^5$ are as defined in respect of formula (Ia).

A specific tubulysin analog-linker compound according to formula (Ia) is represented by formula (Ia-1):

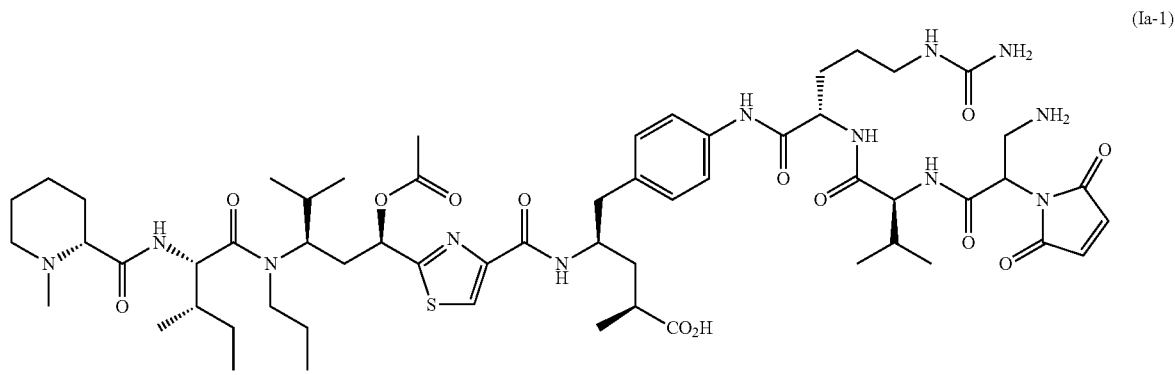 [SMILES: CCCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)[C@H](CCCNC(N)=O)NC(=O)[C@@H](NC(=O)C(CN)N3C(=O)C=CC3=O)C(C)C)cc2)C[C@H](C)C(=O)O)cs1)C(C)C]

(Ia-1)

An ADC prepared with tubulysin analog-linker (Ia-1) is represented by formula (IIa-):

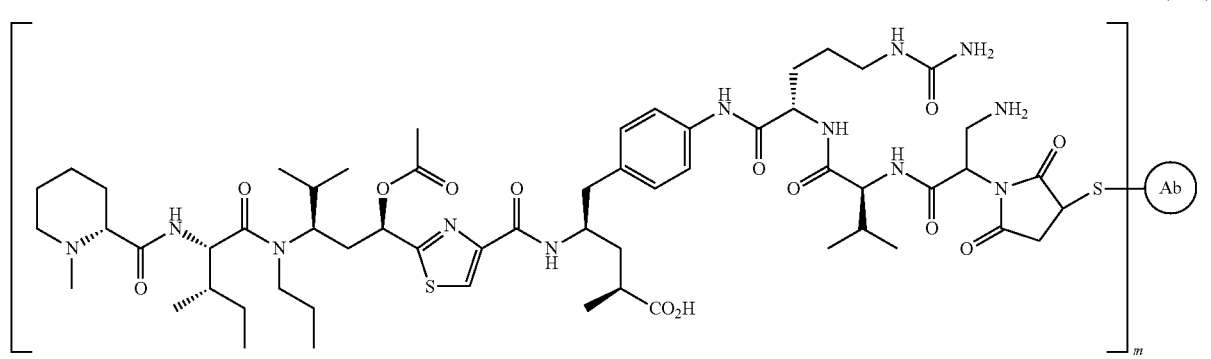

(IIa-1)

wherein
m is 1, 2, 3, or 4 and
Ab is an antibody.

In formula (II) and its derivative formulae, the subscript m denotes the number of tubulysin analog-linkers attached to an antibody. Each antibody can be conjugated with more than one tuubulysin analog-linker, depending on the number thiol groups it has available for conjugation and the experimental conditions employed. Those skilled in the art will appreciate that, while each individual antibody is conjugated to an integer number of tubulysin analog-linkers, an ADC preparation may analyze for a non-integer ratio of tubulysin analog-linker to antibody, reflecting a statistical average. This ratio is referred to as the substitution ratio (SR) or the drug-antibody ratio (DAR).

Antibodies that can be used in conjugates of this invention include those recognizing the following antigens: mesothelin, prostate specific membrane antigen (PSMA), CD19, CD22, CD30, CD70, B7H3, B7H4 (also known as O8E), protein tyrosine kinase 7 (PTK7), glypican-3, RG1, fucosyl-GM1, CTLA-4, and CD44. The antibody can be animal (e.g., murine), chimeric, humanized, or, preferably, human. The antibody preferably is monoclonal, especially a monoclonal human antibody. The preparation of human monoclonal antibodies against some of the aforementioned antigens is disclosed in Korman et al., U.S. Pat. No. 8,609,816 B2 (2013; B7H4, also known as O8E; in particular antibodies 2A7, 1G11, and 2F9); Rao-Naik et al., U.S. Pat. No. 8,097,703 B2 (2012; CD19; in particular antibodies 5G7, 13F1, 46E8, 21D4, 21D4a, 47G4, 27F3, and 3C10); King et al., U.S. Pat. No. 8,481,683 B2 (2013; CD22; in particular antibodies 12C5, 19A3, 16F7, and 23C6); Keler et al., U.S. Pat. No. 7,387,776 B2 (2008; CD30; in particular antibodies 5F11, 2H9, and 17G1); Terrett et al., U.S. Pat. No. 8,124,738 B2 (2012; CD70; in particular antibodies 2H5, 10B4, 8B5, 18E7, and 69A7); Korman et al., U.S. Pat. No. 6,984,720 B1 (2006; CTLA-4; in particular antibodies 10D1, 4B6, and 1E2); Korman et al., U.S. Pat. No. 8,008,449 B2 (2011; PD-1; in particular antibodies 17D8, 2D3, 4H1, 5C4, 4A11, 7D3, and 5F4); Huang et al., US 2009/0297438 A1 (2009; PSMA; in particular antibodies 1C3, 2A10, 2F5, 2C6); Cardarelli et al., U.S. Pat. No. 7,875,278 B2 (2011; PSMA; in particular antibodies 4A3, 7F12, 8C12, 8A11, 16F9, 2A10, 2C6, 2F5, and 1C3); Terrett et al., U.S. Pat. No. 8,222,375 B2 (2012; PTK7; in particular antibodies 3G8, 4D5, 12C6, 12C6a, and 7C8); Harkins et al., U.S. Pat. No. 7,335,748 B2(2008; RG1; in particular antibodies A, B, C, and D); Terrett et al., U.S. Pat. No. 8,268,970 B2 (2012; mesothelin; in particular antibodies 3C10, 6A4, and 7B1); Xu et al., US 2010/0092484 A1 (2010; CD44; in particular antibodies 14G9.B8.B4, 2D1.A3.D12, and 1A9.A6.B9); Deshpande et al., U.S. Pat. No. 8,258,266 B2 (2012; IP10; in particular antibodies 1D4, 1E1, 2G1, 3C4, 6A5, 6A8, 7C10, 8F6, 10A12, 10A12S, and 13C4); Kuhne et al., U.S. Pat. No. 8,450,464 B2 (2013; CXCR4; in particular antibodies F7, F9, D1, and E2); and Korman et al., U.S. Pat. No. 7,943,743 B2 (2011; PD-L1; in particular antibodies 3G10, 12A4, 10A5, 5F8, 10H10, 1B12, 7H1, 11E6, 12B7, and 13G4); the disclosures of which are incorporated herein by reference. Preferably, the antibody is an anti-mesothelin antibody.

While an antibody has numerous cysteine residues, generally all of them are tied up in disulfide bonds, rendering their thiol (—SH) groups unavailable for reaction with a maleimide group in a conjugation reaction.

Various techniques can be introducing a thiol group into an antibody. In a preferred one, an e-amino group in the side chain of a lysine residue in the antibody is reacted with 2-iminothiolane to introduce a free thiol group. The thiol group can react with a maleimide or other nucleophile acceptor group to effect conjugation. Typically, a thiolation level of two to three thiols per antibody is achieved. For a representative procedure, see Cong et al. 2015, the disclosure of which is incorporated herein by reference.

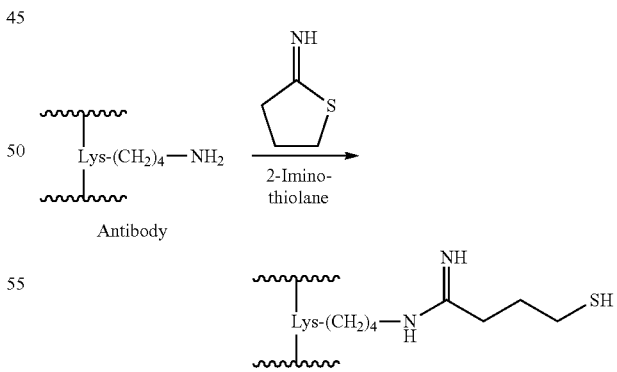

Another method for introducing reactive thiol groups into an antibody is to perform site-specific mutations introducing suitably located cysteine residues. See, e.g., Jununtula et al., Nature Biotechnology 2008, 26 (8), 925; McDonagh et al., U.S. Pat. No. 8,455,622 B2 (2013).

The practice of this invention can be further understood by reference to the following examples, which are provided by way of illustration and not of limitation.

EXAMPLE 1

Stability of ADCs

In this example, the stability of two ADCs, one according to this invention and one not, were compared. ADC (IIa-1') is an ADC according to this invention, where the antibody is anti-mesothelin antibody 6A4 (Terrett et al. 2012, the disclosure of which is incorporated herein by reference). ADC (C) is a comparative ADC (Cheng et al. 2013) with the same tubulysin analog warhead and the same antibody 6A4, but in which the linker lacks a methyleneamino ($CH_2NH_2$) group adjacent to the maleimide group. The heavy chain variable region CDR1, CDR2, and CDR3 of antibody 6A4 are as provided in SEQ ID NO: 1, SEQ ID NO:2, and SEQ ID NO:3, respectively. The kappa chain variable region CDR1, CDR2, and CDR3 of antibody 6A4 are as provided in SEQ NO:4, SEQ ID NO:5, and SEQ ID NO:6, respectively. The heavy and kappa chain variable region amino acid sequences, including framework regions, are shown in FIGS. 3 and 4, respectively, and SEQ ID NO:7 and SEQ ID NO:8, also respectively.

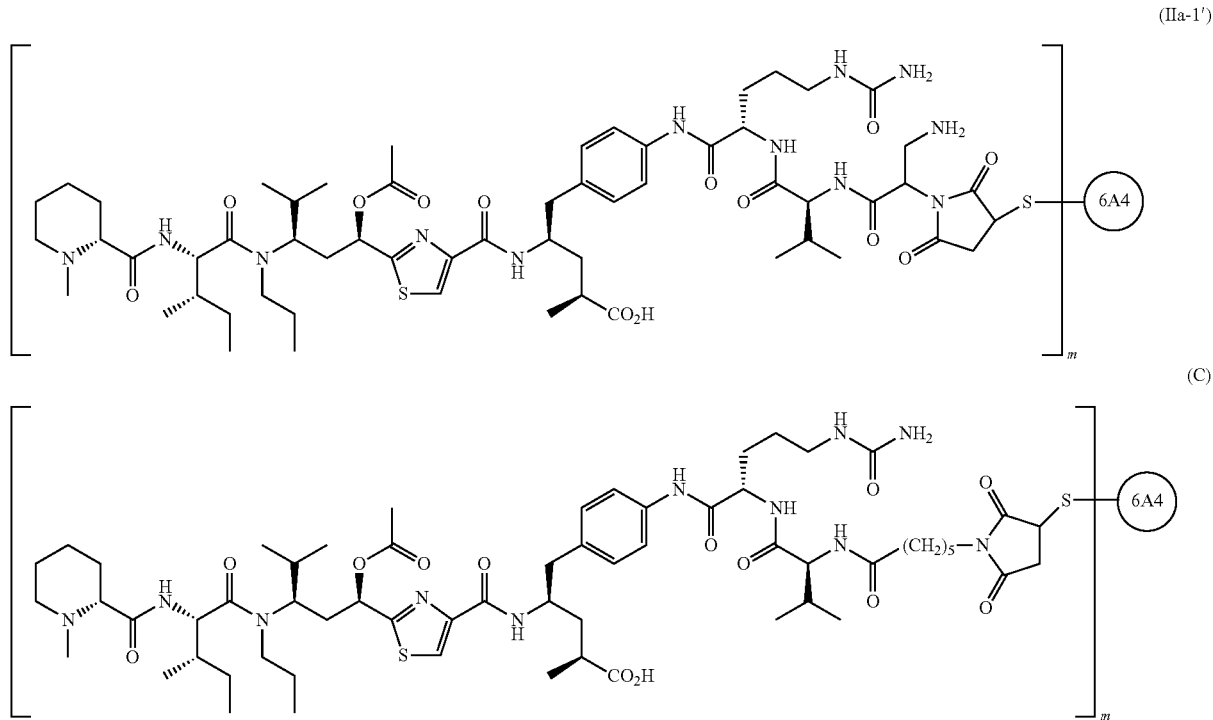

Figure 2:
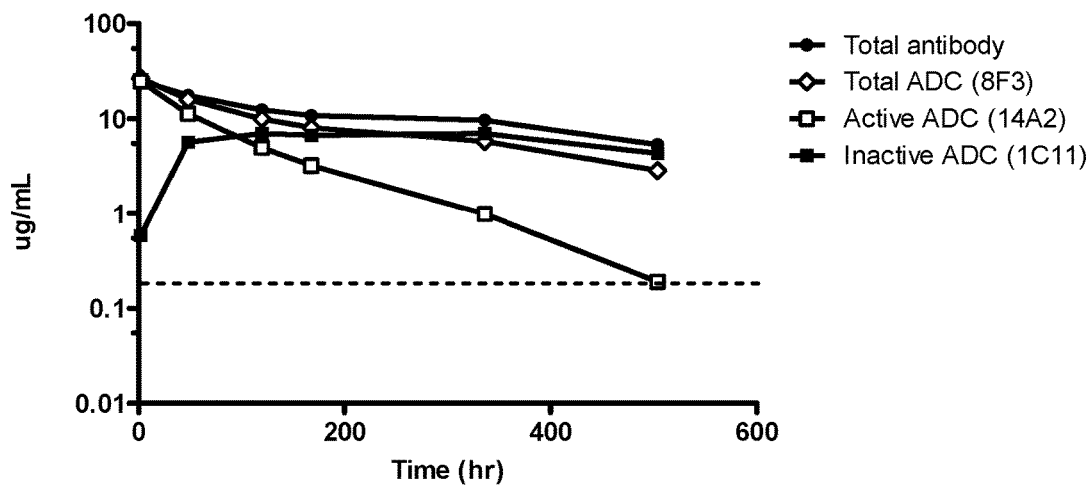
FIG. 2 is a graph showing the in vivo stability of a comparative ADC.

Reference is made to FIG. 1 and FIG. 2 which compare the stabilities of ADCs (IIa-1') and (C). Three antibodies (designated 8F3, 14A2, and 1C11) were prepared and used as analytical reagents for detecting various forms of the ADCs. Antibody 8F3 recognizes the ADC without regard to the acetylation state at the Tuv subunit. Antibody 14A2 recognizes active ADC, that is, ADC in which the Tuv subunit is still acetylated. Lastly, antibody 1C11 recognizes inactive ADC, in which the Tuv subunit has been deacetylated.

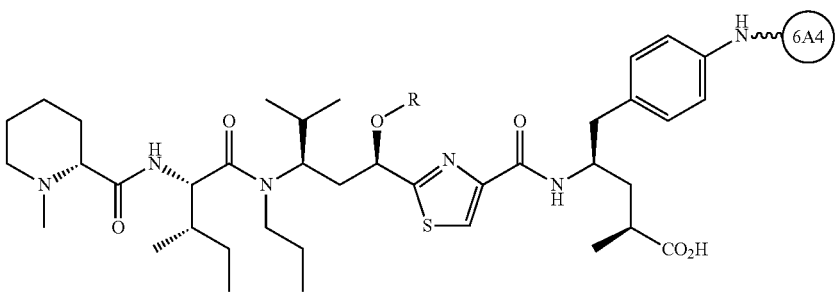

8F3: recognizes either R equals C(=O)CH₃ or H
14A2: recognizes R equals C(=O)CH₃ only
1C11: recognizes R equals H The comparative results from FIGS. 1 and 2 are summarized in Table I.

TABLE I

Comparative Stability of ADCs

| Material Detected | Concentration (μg/mL) at 500 Hr (*) | |
|---|---|---|
| | ADC (IIa-1') | ADC (C) |
| Total antibody | 11 | 6 |
| Total ADC (antibody 8F3) | 11 | 5 |
| Active (acetylated) ADC (antibody 14A2) | 5 | 0.11 |
| Inactive (deacetylated) ADC (antibody 1C11) | 1.3 | 6 |

(*) Determined by ELISA assay using indicated antibody; error margin 20-40%.

At 500 hours, the concentration of active (acetylated) ADC (IIa-1') was about 5 g/mL, while that of inactive (deacetylated) ADC (IIa-1') was about 1.3 μg/mL. That is, ADC (IIa-1') was mostly intact after 500 hours. In contrast, comparative ADC (C) was almost totally converted to the inactive form (6 μg/mL), with only about 0.11 μg/mL of the active form remaining. Thus, the presence of the methyleneamino group in the ADC had a roughly 50-fold effect in protecting the Tuv acetate group against hydrolysis and consequent inactivation of the tubulysin analog.

EXAMPLE 2

Preparation of Tubulysin-Analog Linker (Ia-1)

Figure 5A:
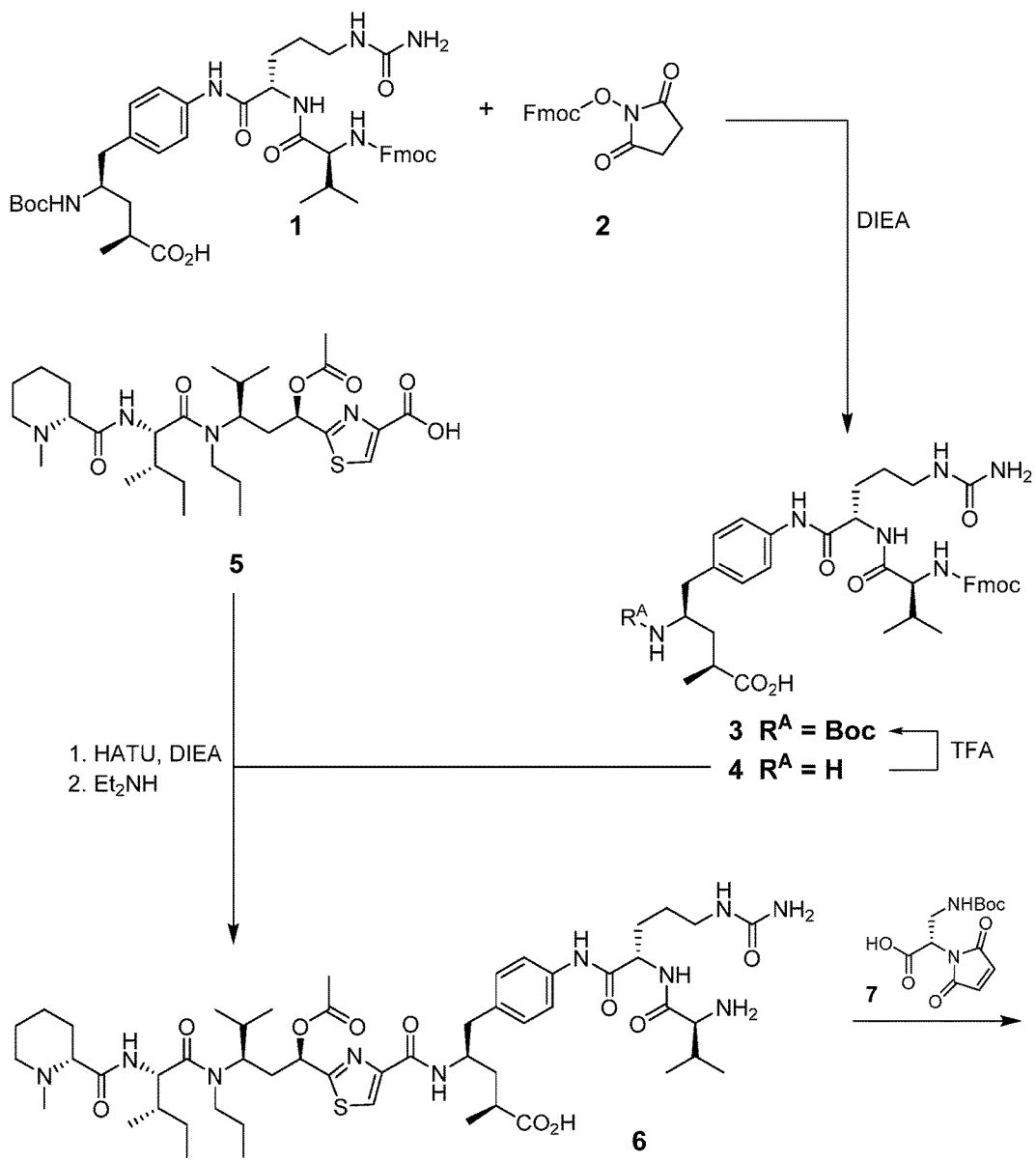
FIGS. 5A and 5B show, in combination, a scheme for the synthesis of compound (Ia-1), as described in further detail in Example 2 hereinbelow.
Figure 5B:
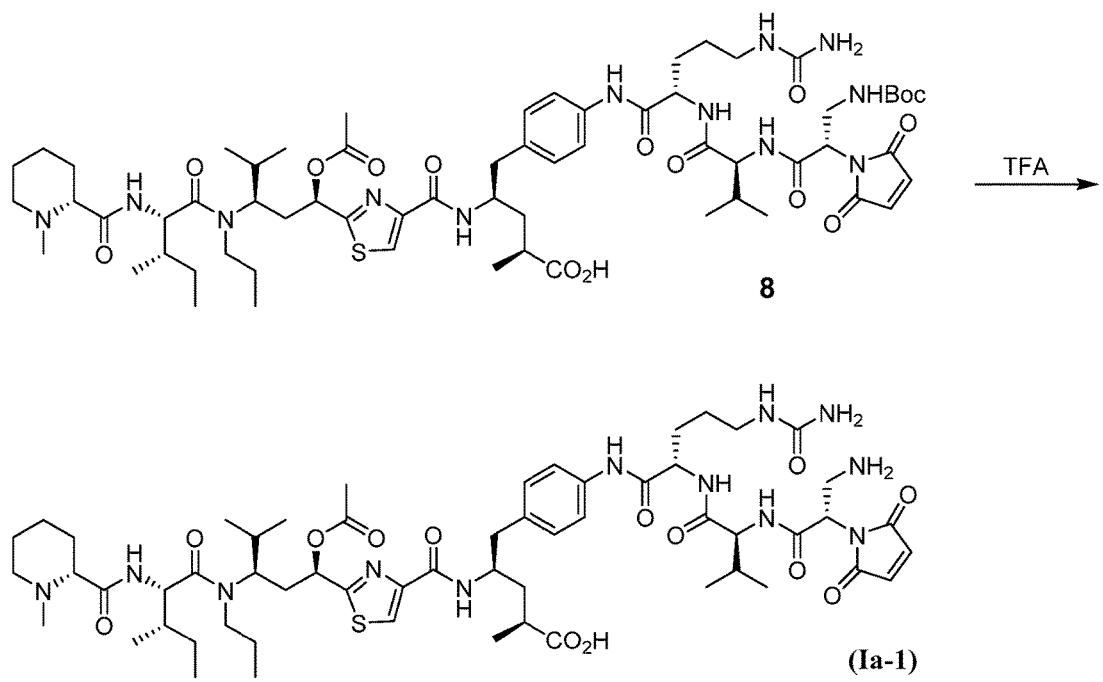

This example relates to the synthesis of compound (Ia-1), with reference to FIGS. 5A and 5B.

Compound 2 (CAS Reg. No. 82911-69-1, available from Chem-Impex, 87.0 mg, 0.257 mmol) and N,N-diisopropylethylamine (DIEA, 40.9 μL, 0.234 mmol) were added into a solution of compound 1 (Cong et al. 2015; 135.4 mg, 0.234 mmol) in N,N-dimethylformamide (DMF, 2 mL) at room temperature (RT). After 10 min, 3 mL of 10% formic acid and 30 mL water were added to cause white precipitate to form. After filtration, the precipitate was washed with dichloromethane (DCM) to give compound 3 (138.0 mg, 0.162 mmol, 69.2% yield, purity by HPLC 94%). MS: (+) m/z, 801.4 (M+1).

Compound 3 (138.0 mg, 0.162 mmol, 94% purity) was suspended in a 3 mL mixture of DCM and trifluoroacetic acid (TFA), 1:1, at RT. After 2 min the mixture was evaporated to give compound 4 (138 mg, 0.197 mmol, the yield assumed to be 100% and extra weight assumed to be TFA). MS: (+) m/z, 701.4 (M+1).

N,N,N',N'-tetramethyl-O-(7-azabenzotriazol-1-yl)uronium hexafluorophosphate (HATU, 730.0 μL, 0.162 mmol, 222 mM in DMF) and DIEA (70.7 μL, 0.405 mmol) were added to a solution of compound 5 (Cheng et al. 2013, 1246 μL, 0.162 mmol, 130 mM in DMF) at 5° C. After stirring at RT for 10 min, the mixture was added to a DMF (1.2 mL) solution of Compound 4 (114 mg, 0.162 mmol) with DIEA (180 uL, 1.03 mmol) at RT. After 10 min at RT, diethylamine (118 μL, 1.134 mmol) was added at 5° C. and the mixture was stirred for 20 min. The reaction mixture was quenched with 10% formic acid and taken up in DMSO and purified by preparative chromatography. After evaporation of the fractions, compound 6 (49 mg, 0.045 mmol, 28.0% yield) was obtained as a white solid. MS: (+) m/z, 1027.7 (M+1). Preparative chromatography conditions: Column: XBridge BEH Shield RP18 OBD Prep Column, 130 Å, 5 μm, 30 mm×150 mm, 1/pkg [186002990], flow rate: 40 mL/min, 23 min gradient: 20-40%, acetonitrile (with 0.1% TFA)/water (with 0.1% TFA). Fractions were collected at 33% acetonitrile in water.

Compound 7 was synthesized as follows:

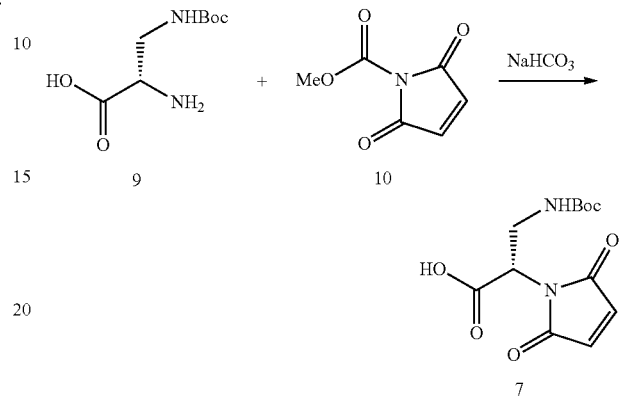

Compound 10 (CAS Reg. No. 73259-81-1, available from Chem-Impex, 50.0 mg, 0.245 mmol) was dissolved in 2 mL saturated sodium bicarbonate solution at RT. Compound 9 (CAS Reg. No. 55750-48-6, available from Sigma-Aldridge, 38.0 mg, 0.245 mmol) was added at 5° C. It took about 10 min for the suspension to become homogeneous and the reaction vessel was left in a freezer overnight. The mixture was acidified with 10% TFA and purified by preparative chromatography to give compound 7 (25.0 mg, 0.088 mmol, 35.9% yield) as a mixture of rotamers. MS: (+) m/z, 284.9 (M+1). For the major rotamer: $^1$H NMR (400 MHz, METHANOL-$d_4$) δ ppm 1.38 (s, 9 H), 3.56-3.66 (m, 1 H), 3.69-3.80 (m, 1 H), 4.80 (dd, J=10.4, 4.3 Hz, 1 H), 6.87 (s, 2 H). Preparative chromatography conditions: Column: XBridge BEH Shield RP18 OBD Prep Column, 130 Å, 5 m, 30 mm×150 mm, 1/pkg [186002990], flow rate: 40 mL/min, 23 min gradient: 5-50%, acetonitrile (with 0.1% TFA)/water (with 0.1% TFA). Fractions were collected at 20% acetonitrile in water.

HATU (95 μL, 0.021 mmol, 222 mM in DMF) and DIEA (11.06 μL, 0.063 mmol) were added compound 7 (243 μL, 0.021 mmol, 87 mM in DMF) at 5° C. After stirring for 10 min at RT, the solution was added to a solution of compound 6 (310 μL, 0.013 mmol, 40.9 mM in DMF) with DIEA (11.06 μL, 0.063 mmol) at RT. After 10 min, the mixture was acidified with 10% formic acid at 5° C. The mixture was then taken up in DMSO. The reaction was repeated three more times and all the DMSO solutions were combined and purified by preparative chromatography. After lyophilization, compound 8 (17.5 mg, 0.014 mmol, 27% yield) was obtained as a mixture of rotamers. MS: (+) m/z, 1293.7 (M+1). Preparative chromatography conditions: Column: XBridge BEH C18 OBD Prep Column, 130 Å, 5 μm, 30 mm×150 mm, 1/pkg [186003284] Gradient: flow rate: 40 mL/min, 0-2 min: 20%, 2-5 min: 20-30%, 5-23 min: 30-50%, 23-24 min: 50-95%, 24-28 min: 95%, 28-28.1 min: 95-20%, 28.1-30 min: 20%. acetonitrile (with 0.1% TFA)/water (with 0.1% TFA). Fractions collected at 40% acetonitrile in water.

Compound 8 (17.5 mg, 0.014 mmol) was dissolved in a 1 mL mixture of DCM and TFA (1:1) at 5° C. After 20 min, the volatiles were removed by evaporation and the residue was purified by preparative chromatography. After lyophilization, two rotational isomers of compound (Ia-1) (5.0 mg, 27.6% yield; 11.8 mg, 72.3%) were obtained. MS: (+) m/z, 1193.7 (M+1). The pure minor isomer was conjugated to antibody. Preparative chromatography conditions: Column: XBridge BEH C18 OBD Prep Column, 130 Å, 5 μm, 30 mm×150 mm, 1/pkg [186003284] Gradient: flow rate: 40 mL/min, 0-2 min: 5%, 2-5 min: 5-20%, 5-23 min: 20-40%, 23-24 min: 40-95%, 24-28 min: 95%, 28-28.1 min: 95-5%, 28.1-30 min: 5%. acetonitrile (with 0.1% TFA)/water (with 0.1% TFA). Minor rotamer was collected at 36% acetonitrile in water; major rotamer was collected at 37% acetonitrile in water.

EXAMPLE 3

Preparation of ADCs

This general procedure is based on introduction of free thiol groups into an antibody by reaction of lysine e-amino groups with 2-iminothiolane, followed by reaction with a maleimide-containing drug-linker moiety, such as described above. Initially the antibody is buffer exchanged into 0.1 M phosphate buffer (pH 8.0) containing 50 mM NaCl and 2 mM diethylene triamine pentaacetic acid (DTPA) and concentrated to 5-10 mg/mL. Thiolation is achieved through addition of 2-iminothiolane to the antibody. The amount of 2-iminothiolane to be added can be determined by a preliminary experiment and varies from antibody to antibody. In the preliminary experiment, a titration of increasing amounts of 2-iminothiolane is added to the antibody, and following incubation with the antibody for 1 h at RT (room temperature, circa 25° C.), the antibody is desalted into 50 mM HEPES, 5 mM Glycine, 2 mM DTPA, pH 5.5 using a SEPHADEX™ G-25 column and the number of thiol groups introduced determined rapidly by reaction with dithiodipyridine (DTDP). Reaction of thiol groups with DTDP results in liberation of thiopyridine, which can be monitored spectroscopically at 324 nm. Samples at a protein concentration of 0.5-1.0 mg/mL are typically used. The absorbance at 280 nm can be used to accurately determine the concentration of protein in the samples, and then an aliquot of each sample (0.9 mL) is incubated with 0.1 mL DTDP (5 mM stock solution in ethanol) for 10 min at RT. Blank samples of buffer alone plus DTDP are also incubated alongside. After 10 min, absorbance at 324 nm is measured and the number of thiol groups is quantitated using an extinction coefficient for thiopyridine of 19,800 $M^{-1}$.

Typically a thiolation level of about two to three thiol groups per antibody is desirable. For example, with some antibodies this can be achieved by adding a 15-fold molar excess of 2-iminothiolane followed by incubation at RT for 1 h. The antibody is then incubated with 2-iminothiolane at the desired molar ratio and then desalted into conjugation buffer (50 mM HEPES, 5 mM glycine, 2 mM DTPA, pH 5.5)). The thiolated material is maintained on ice while the number of thiols introduced is quantitated as described above.

After verification of the number of thiols introduced, the drug (dimer)-linker moiety is added at a 2.5-fold molar excess per thiol. The conjugation reaction is allowed to proceed in conjugation buffer containing a final concentration of 25% propylene glycol and 5% trehalose. Commonly, the drug-linker stock solution is dissolved in 100% DMSO. The stock solution is added directly to the thiolated antibody.

The conjugation reaction mixture is incubated at RT for 2 h with gentle stirring. A 10-fold molar excess of N-ethyl maleimide (100 mM Stock in DMSO) is then added to the conjugation mixture and stirred for an additional hour to block any unreacted thiols.

The sample is then filtered via a 0.2μ filter The material is buffer exchanged via TFF VivaFlow 50 Sartorius 30 MWCO PES membrane into 10 mg/mL glycine, 20 mg/mL sorbitol, 15% acetonitrile pH 5.0 (5×TFF buffer exchange volume), to remove any unreacted drug. The final formulation is carried out by TFF into 20 mg/mL sorbitol, 10 mg/mL glycine, pH 5.0.

EXAMPLE 4

Antibodies 8F3, 14A2, and 1C11

Monoclonal antibodies 8F3 and 14A2 were generated by immunizing Balb/C mice with a conjugate of compound (III) and keyhole limpet hemocyanin (KLH). Compound (III) is derived from the natural product tubulysin D.

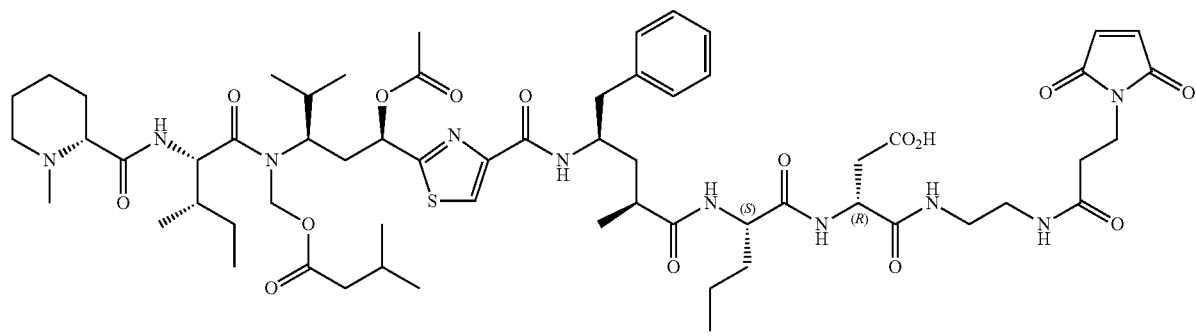

(III)

Monoclonal antibody 1C11 was generated by immunizing Balb/C mice with a KLH conjugate of compound (IV), which is a synthetic tubulysin analog.

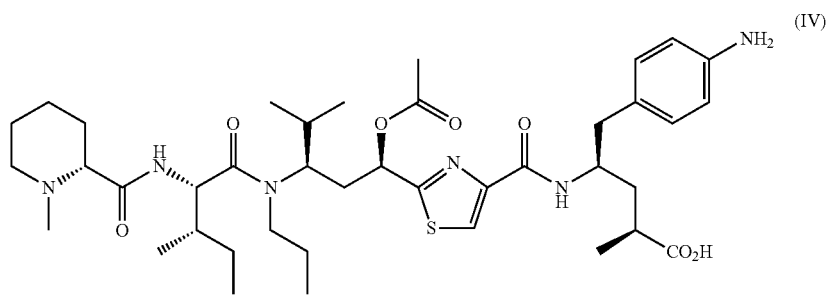 [SMILES: CCCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(N)cc2)C[C@H](C)C(=O)O)cs1)C(C)C]

(IV)

The antigenic specificities of antibodies 8F3, 14A2, and 1C11 were determined using ELISA, testing against compound (V) or its deacetylated product (V').

invention is not limited to such preferred embodiments. Rather, the scope of the invention is defined by the appended claims.

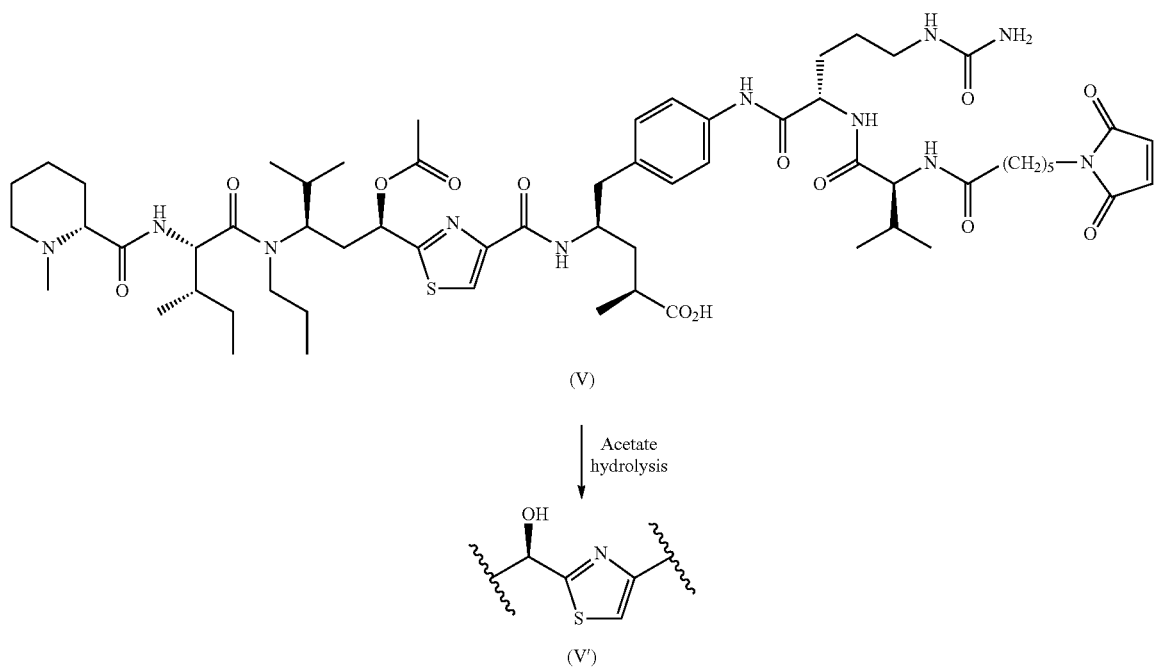

It was found that antibody 8F3 recognized both compounds (V) and (V'); antibody 14A2 recognized only compound (V); and that antibody 1C11 recognized only compound (V').

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the

REFERENCES

Full citations for the following references cited in abbreviated fashion by first author (or inventor) and date earlier in this specification are provided below. Each of these references is incorporated herein by reference for all purposes.

Balasubramanian et al., *J. Med. Chem.* 2009, 52 (2), 238-240.
Cheng et al., U.S. Pat. No. 8,394,922 B2 (2013).
Cong et al., U.S. Pat. No. 8,980,824 B2 (2015).
Domling et al., *Ang. Chem. Int. Ed.* 2006, 45, 7235-7239.
Junutula et al., *Nature Biotechnology* 2008, 26 (8), 925.
Khalil et al., *ChemBioChem* 2006, 7, 678.
Kaur et al., *Biochem. J.* 2006, 396, 235-242.
Lyon et al., US 2013/0309256 A1 (2013).
Lyon et al., WO 2015/057699 A2 (2015).
Schrama et al., *Nature Rev. Drug Disc.* 2006, 5, 147-159.
Terrett et al., U.S. Pat. No. 8,268,970 B2 (2012).

TABLE OF SEQUENCES

TABLE II

Sequence Summary

| SEQ ID NO: | SEQUENCE DESCRIPTION |
|---|---|
| 1 | 6A4 Heavy chain CDR1 a.a. |
| 2 | 6A4 Heavy chain CDR2 a.a. |
| 3 | 6A4 Heavy chain CDR3 a.a. |
| 4 | 6A4 Kappa chain CDR1 a.a. |
| 5 | 6A4 Kappa chain CDR2 a.a. |
| 6 | 6A4 Kappa chain CDR3 a.a. |
| 7 | 6A4 Heavy chain variable region a.a. |
| 8 | 6A4 Kappa chain variable region a.a. |

What is claimed is:

1. A tubulysin analog-linker compound having a structure represented by formula (I)

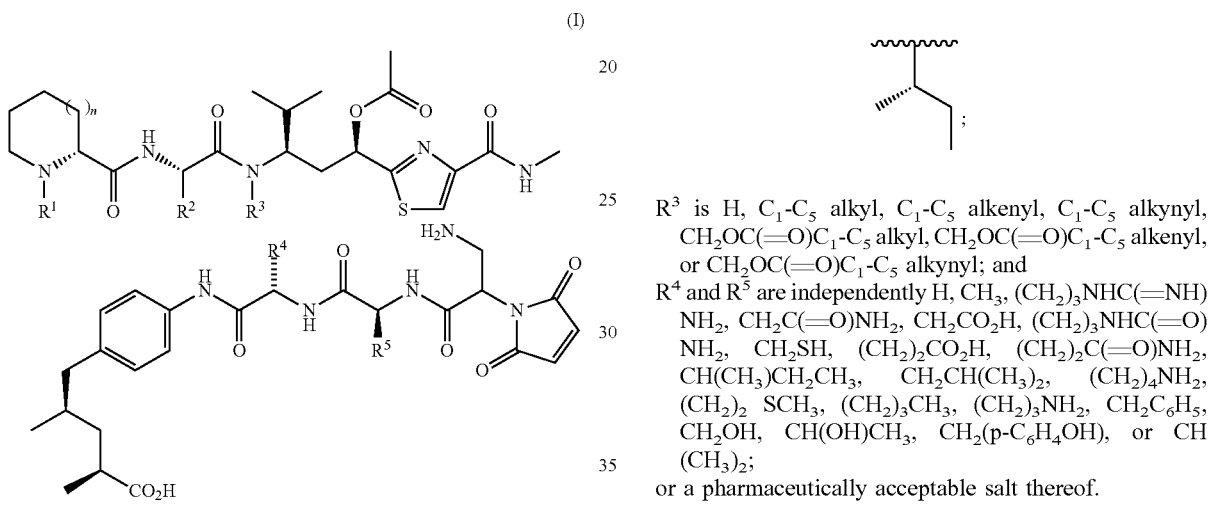

wherein n is 0, 1, or 2;

$R^1$ is H, Me, Et, or n-Pr;

$R^2$ is Me, Et, $CH_2CH_2CH_3$, $CH(Me)_2$, $CH(Et)_2$, or

[structure];

$R^3$ is H, $C_1$-$C_5$ alkyl, $C_1$-$C_5$ alkenyl, $C_1$-$C_5$ alkynyl, $CH_2OC(=O)C_1$-$C_5$ alkyl, $CH_2OC(=O)C_1$-$C_5$ alkenyl, or $CH_2OC(=O)C_1$-$C_5$ alkynyl; and $R^4$ and $R^5$ are independently H, $CH_3$, $(CH_2)_3NHC(=NH)NH_2$, $CH_2C(=O)NH_2$, $CH_2CO_2H$, $(CH_2)_3NHC(=O)NH_2$, $CH_2SH$, $(CH_2)_2CO_2H$, $(CH_2)_2C(=O)NH_2$, $CH(CH_3)CH_2CH_3$, $CH_2CH(CH_3)_2$, $(CH_2)_4NH_2$, $(CH_2)_2SCH_3$, $(CH_2)_3CH_3$, $(CH_2)_3NH_2$, $CH_2C_6H_5$, $CH_2OH$, $CH(OH)CH_3$, $CH_2(p-C_6H_4OH)$, or $CH(CH_3)_2$;

or a pharmaceutically acceptable salt thereof.

2. A tubulysin analog-linker compound according to claim 1, having a structure represented by formula (Ia)

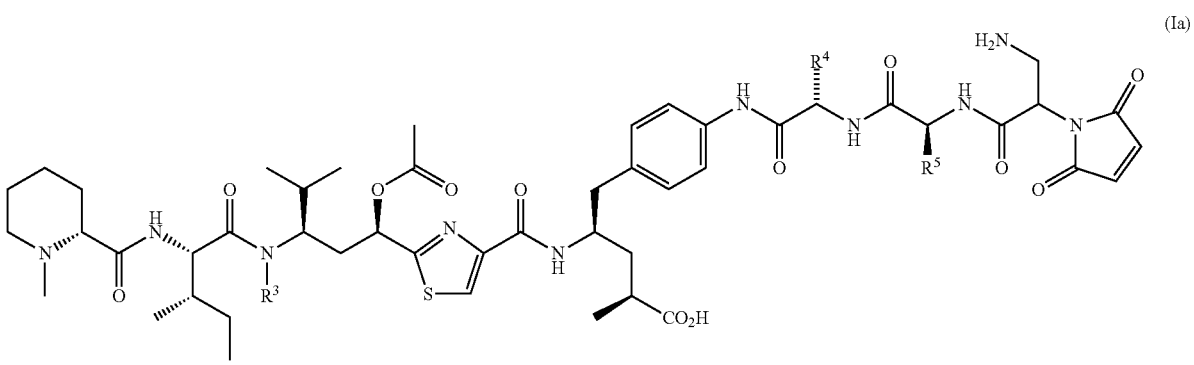

wherein $R^3$ is $C_1$-$C_3$ alkyl; and $R^4$ and $R^5$ are independently $CH(CH_3)_2$, $CH_3$, $(CH_2)_3NHC(=O)NH_2$, or $(CH_2)_4NH_2$.

3. A tubulysin analog-linker according to claim 2, wherein $R^3$ is $CH_3$ or $CH_2CH_2CH_3$.

4. A tubulysin analog-linker according to claim 3, wherein $R^4$ equals $(CH_2)_3NHC(=O)NH_2$ and $R^5$ equals $CH(CH_3)_2$ or $R^4$ equals $CH_3$ and $R^5$ equals $CH(CH_3)_2$.

5. A tubulysin analog-linker according to claim 1, having a structure represented by formula (Ia-1):

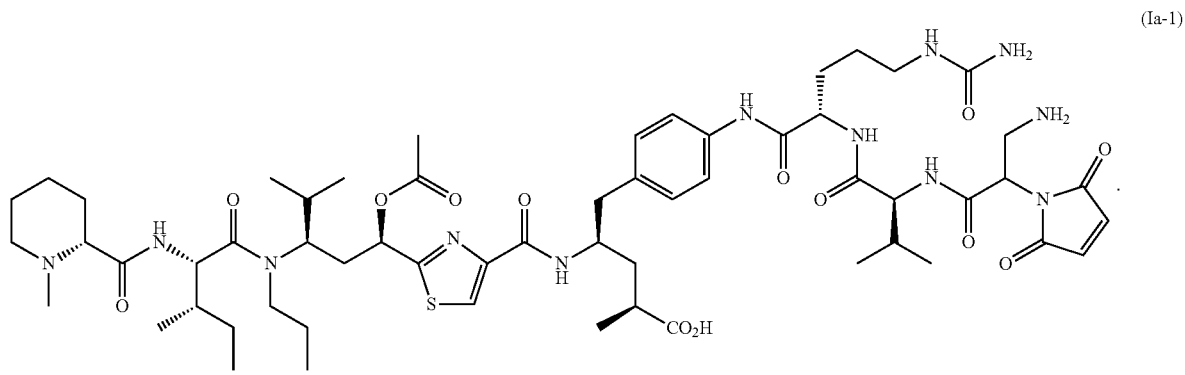 [SMILES: CCCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)[C@H](CCCNC(N)=O)NC(=O)[C@@H](NC(=O)C(CN)N3C(=O)C=CC3=O)C(C)C)cc2)C[C@H](C)C(=O)O)cs1)C(C)C]
(Ia-1)

6. An antibody-drug conjugate, having a structure represented by formula (II)

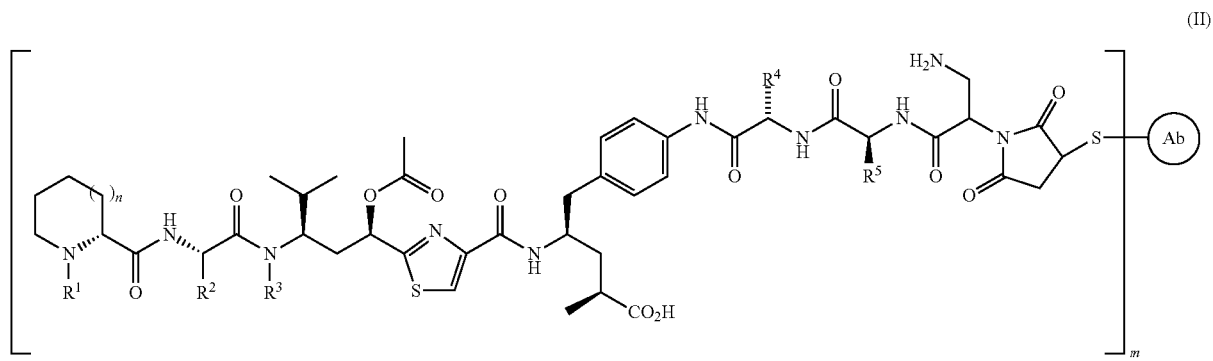
(II)

wherein
m is 1, 2, 3, or 4;
Ab is an antibody;
n is 0, 1, or 2;
$R^1$ is H, Me, Et, or n-Pr;
$R^2$ is Me, Et, $CH_2CH_2CH_3$, $CH(Me)_2$, $CH(Et)_2$, or

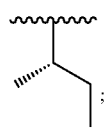
;

$R^3$ is H, $C_1$-$C_5$ alkyl, $C_1$-$C_5$ alkenyl, $C_1$-$C_5$ alkynyl, $CH_2OC(=O)C_1$-$C_5$ alkyl, $CH_2OC(=O)C_1$-$C_5$ alkenyl, or $CH_2OC(=O)C_1$-$C_5$ alkynyl; and $R^4$ and $R^5$ are independently H, $CH_3$, $(CH_2)_3NHC(=NH)NH_2$, $CH_2C(=O)NH_2$, $CH_2CO_2H$, $(CH_2)_3NHC(=O)NH_2$, $CH_2SH$, $(CH_2)_2CO_2H$, $(CH_2)_2C(=O)NH_2$, $CH(CH_3)CH_2CH_3$, $CH_2CH(CH_3)_2$, $(CH_2)_4NH_2$, $(CH_2)_2SCH_3$, $(CH_2)_3CH_3$, $(CH_2)_3NH_2$, $CH_2C_6H_5$, $CH_2OH$, $CH(OH)CH_3$, $CH_2(p-C_6H_4OH)$, or $CH(CH_3)_2$.

7. An antibody-drug conjugate according to claim 6, having a structure represented by formula (IIa)

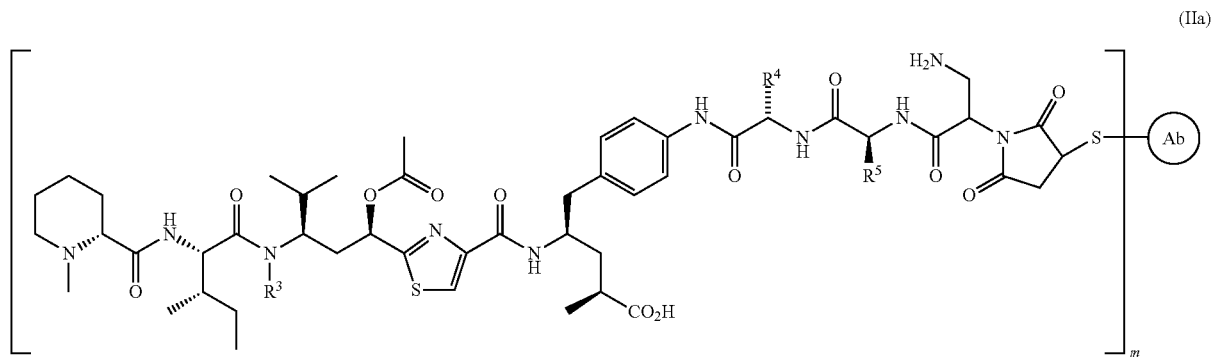
(IIa)

wherein
m is 1, 2, 3, or 4;
Ab is an antibody;
$R^3$ is $C_1$-$C_3$ alkyl; and
$R^4$ and $R^5$ are independently $CH(CH_3)_2$, $CH_3$, $(CH_2)_3NHC(=O)NH_2$, or $(CH_2)_4NH_2$.

8. An antibody-drug conjugate according to claim 7, wherein $R^3$ is $CH_3$ or $CH_2CH_2CH_3$.

9. An antibody-drug conjugate according to claim 7, wherein $R^4$ equals $(CH_2)_3NHC(=O)NH_2$ and $R^5$ equals $CH(CH_3)_2$ or $R^4$ equals $CH_3$ and $R^5$ equals $CH(CH_3)_2$.

10. An antibody-drug conjugate according to claim 7, wherein the antibody is an anti-mesothelin antibody.

11. An antibody-drug conjugate according to claim 10, wherein the anti-mesothelin antibody is antibody 6A4, having:
    (a) a heavy chain variable region CDR1 comprising SEQ ID NO: 1;
    (b) a heavy chain variable region CDR2 comprising SEQ ID NO:2;
    (c) a heavy chain variable region CDR3 comprising SEQ ID NO:3;
    (d) a kappa chain variable region CDR1 comprising sequence ID NO:4;
    (e) a kappa chain variable region CDR2 comprising sequence ID NO: 5; and
    (f) a kappa chain variable region CDR3 comprising sequence ID NO: 6.

12. An antibody-drug conjugate according to claim 7, having a structure represented by formula (IIa-1)

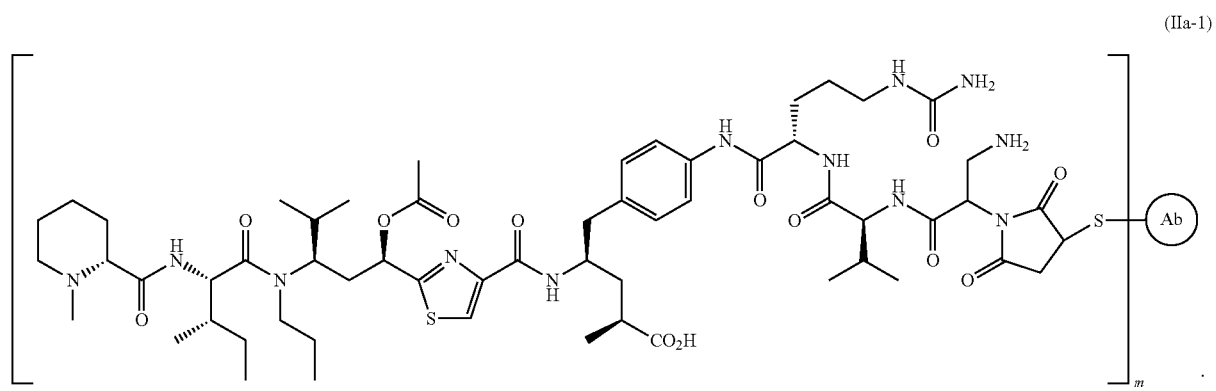

(IIa-1)

13. An antibody-drug conjugate according to claim 11, wherein the antibody is an anti-mesothelin antibody.

14. An antibody-drug conjugate according to claim 13, wherein the anti-mesothelin antibody is antibody 6A4, having:
    (a) a heavy chain variable region CDR1 comprising SEQ ID NO: 1;
    (b) a heavy chain variable region CDR2 comprising SEQ ID NO:2;
    (c) a heavy chain variable region CDR3 comprising SEQ ID NO:3;
    (d) a kappa chain variable region CDR1 comprising sequence ID NO:4;
    (e) a kappa chain variable region CDR2 comprising sequence ID NO: 5; and
    (f) a kappa chain variable region CDR3 comprising sequence ID NO: 6.

15. A pharmaceutical composition comprising an antibody-drug conjugate according to claim 7 and a pharmaceutically acceptable excipient.

* * * * *

SEQUENCE LISTING

```
<160> NUMBER OF SEQ ID NOS: 8

<210> SEQ ID NO 1
<211> LENGTH: 5
<212> TYPE: PRT
<213> ORGANISM: Homo sapiens

<400> SEQUENCE: 1

Ile Tyr Gly Met His
1               5

<210> SEQ ID NO 2
<211> LENGTH: 17
<212> TYPE: PRT
<213> ORGANISM: Homo sapiens

<400> SEQUENCE: 2

Val Leu Trp Tyr Asp Gly Ser His Glu Tyr Tyr Ala Asp Ser Val Lys
1               5                   10                  15

Gly

<210> SEQ ID NO 3
<211> LENGTH: 13
<212> TYPE: PRT
<213> ORGANISM: Homo sapiens

<400> SEQUENCE: 3

Asp Gly Asp Tyr Tyr Asp Ser Gly Ser Pro Leu Asp Tyr
1               5                   10

<210> SEQ ID NO 4
<211> LENGTH: 11
<212> TYPE: PRT
<213> ORGANISM: Homo sapiens

<400> SEQUENCE: 4

Arg Ala Ser Gln Ser Val Ser Ser Tyr Leu Ala
1               5                   10

<210> SEQ ID NO 5
<211> LENGTH: 7
<212> TYPE: PRT
<213> ORGANISM: Homo sapiens

<400> SEQUENCE: 5

Asp Ala Ser Asn Arg Ala Thr
1               5

<210> SEQ ID NO 6
<211> LENGTH: 9
<212> TYPE: PRT
<213> ORGANISM: Homo sapiens
```

```
<400> SEQUENCE: 6

Gln Gln Arg Ser Asn Trp Pro Leu Thr
1               5

<210> SEQ ID NO 7
<211> LENGTH: 122
<212> TYPE: PRT
<213> ORGANISM: Homo sapiens
<220> FEATURE:
<221> NAME/KEY: MISC_FEATURE
<222> LOCATION: (31)..(35)
<223> OTHER INFORMATION: VH CDR1
<220> FEATURE:
<221> NAME/KEY: MISC_FEATURE
<222> LOCATION: (50)..(66)
<223> OTHER INFORMATION: VH CDR2
<220> FEATURE:
<221> NAME/KEY: MISC_FEATURE
<222> LOCATION: (99)..(111)
<223> OTHER INFORMATION: VH CDR3

<400> SEQUENCE: 7

Gln Val His Leu Val Glu Ser Gly Gly Gly Val Val Gln Pro Gly Arg
1               5                   10                  15

Ser Leu Arg Leu Ser Cys Val Ala Ser Gly Ile Thr Phe Arg Ile Tyr
            20                  25                  30

Gly Met His Trp Val Arg Gln Ala Pro Gly Lys Gly Leu Glu Trp Val
        35                  40                  45

Ala Val Leu Trp Tyr Asp Gly Ser His Glu Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Asp Gly Asp Tyr Tyr Asp Ser Gly Ser Pro Leu Asp Tyr Trp
            100                 105                 110

Gly Gln Gly Thr Leu Val Thr Val Ser Ser
        115                 120

<210> SEQ ID NO 8
<211> LENGTH: 107
<212> TYPE: PRT
<213> ORGANISM: Homo sapiens
<220> FEATURE:
<221> NAME/KEY: MISC_FEATURE
<222> LOCATION: (24)..(34)
<223> OTHER INFORMATION: VK CDR1
<220> FEATURE:
<221> NAME/KEY: MISC_FEATURE
<222> LOCATION: (50)..(56)
<223> OTHER INFORMATION: VK CDR2
<220> FEATURE:
<221> NAME/KEY: MISC_FEATURE
<222> LOCATION: (89)..(97)
<223> OTHER INFORMATION: VK CDR3

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
```

```
                50                      55                      60
Ser Gly Ser Gly Thr Asp Phe Thr Leu Thr Ile Ser Ser Leu Glu Pro
 65                      70                      75                      80

Glu Asp Phe Ala Val Tyr Tyr Cys Gln Gln Arg Ser Asn Trp Pro Leu
                         85                      90                      95

Thr Phe Gly Gly Gly Thr Lys Val Glu Ile Lys
                100                     105
```